United States Patent
Berthon-Jones et al.

(10) Patent No.: US 6,445,942 B1
(45) Date of Patent: Sep. 3, 2002

(54) MEASUREMENT OF RESPIRATORY EFFORT USING A SUPRASTERNAL SENSOR

(76) Inventors: Michael Berthon-Jones, 7 Leonav Parade, Leonay NSW 2750 (AU); Gordon Joseph Malouf, 6/108 Brook Street, Coogee NSW 2034 (AU); Peter Edward Bateman, 17s Tripod Street, Concord NSW 2137 (AU)

( * ) Notice: Subject to any disclaimer, the term of this patent is extended or adjusted under 35 U.S.C. 154(b) by 0 days.

(21) Appl. No.: 09/396,032

(22) Filed: Sep. 15, 1999

(51) Int. Cl.$^7$ .................................................. A61B 5/08
(52) U.S. Cl. .......................... 600/407; 600/473; 600/534
(58) Field of Search ................................. 600/473, 475, 600/476, 477, 529, 533, 534, 536, 407

(56) References Cited

U.S. PATENT DOCUMENTS

| | | | |
|---|---|---|---|
| 3,913,563 A | * 10/1975 | Ball | 600/534 |
| 4,180,059 A | 12/1979 | Tiep | |
| 4,660,568 A | * 4/1987 | Cosman | 600/534 |
| 5,195,536 A | * 3/1993 | Silva et al. | 600/534 |
| 5,316,010 A | * 5/1994 | Brown | 600/534 |
| 5,791,349 A | * 8/1998 | Shmulewitz | 600/547 |
| 6,095,987 A | * 8/2000 | Shmulewitz et al. | 600/547 |
| 6,292,689 B1 | * 9/2001 | Wallace et al. | 600/547 |

* cited by examiner

*Primary Examiner*—Ruth S. Smith
(74) *Attorney, Agent, or Firm*—Gottlieb, Rackman & Reisman, P.C.

(57) ABSTRACT

The invention is an optical sensor whose output represents or measures movement of the skin of the suprasternal notch, this movement being a measure of respiratory effort. The use of a trough detector, with a time constant long compared with a breath but short compared with the interval between changes in body position, allows detection of the optical signal corresponding to zero effort. Subtraction of the trough signal from the optical signal produces a self-zeroing effort signal which automatically compensates for changes in body position. A soft, low irritant adhesive material, which may be left in place on the skin for several days, allows the sensor to be placed and removed as often as desired without injuring the skin.

23 Claims, 6 Drawing Sheets

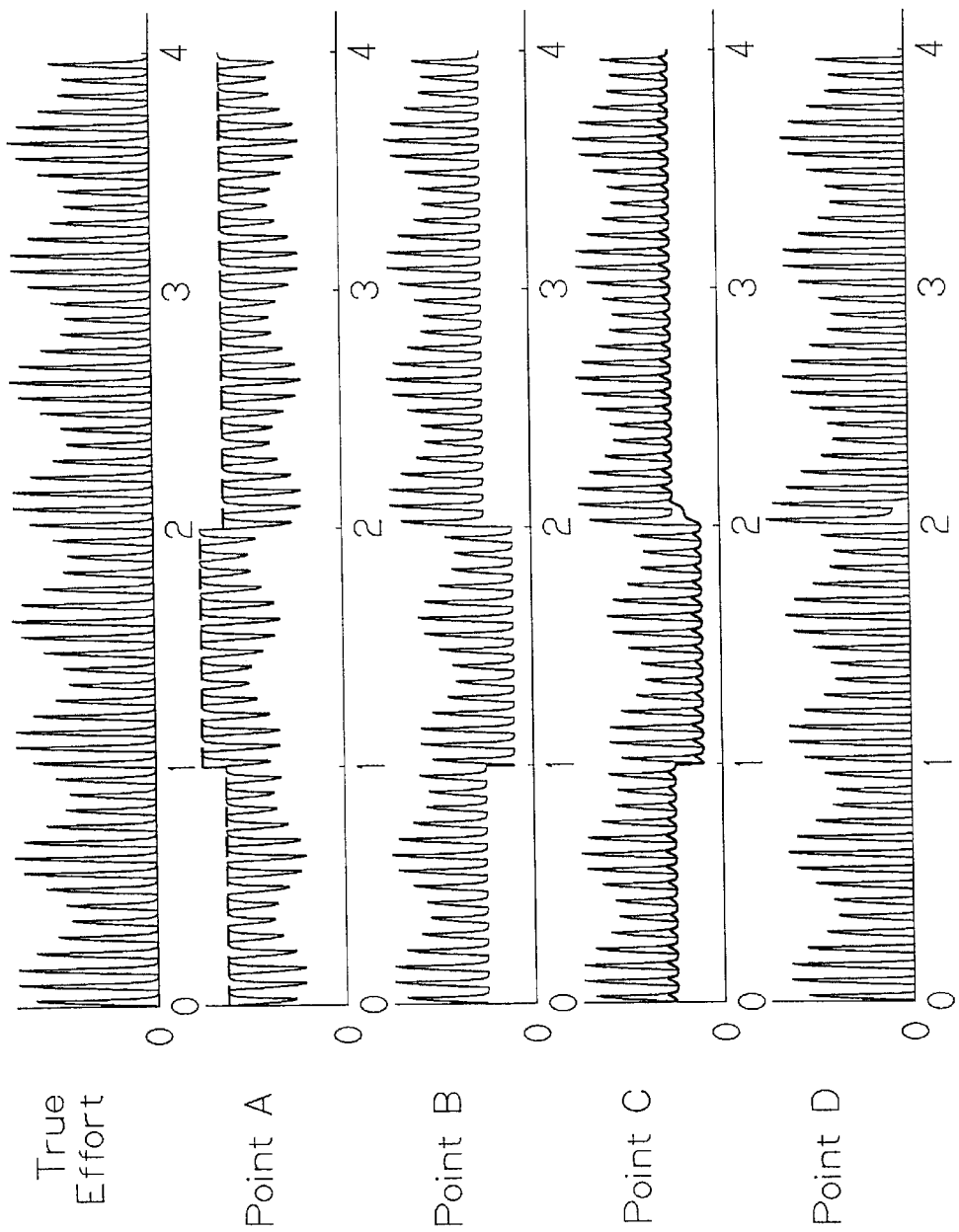

MEASUREMENT OF RESPIRATORY EFFORT USING A SUPRASTERNAL SENSOR

FIELD OF THE INVENTION

This invention pertains to the noninvasive measurement of respiratory muscular effort such as might be useful, for example, in control of the triggering of a mechanical ventilator.

BACKGROUND

It is useful to be able to measure respiratory effort for a number of purposes, including determining when and by how much a subject is attempting to breathe; detecting a central apnea or hypopnea, increased upper airway resistance or obstructive sleep apnea; and triggering of mechanical ventilators.

The prior art includes the direct invasive measurement of pleural pressure, for example, by using a pressure sensor in the pleural cavity or esophagus, or using an esophageal balloon connected to a pressure transducer; or measurement of transdiaphragmatic pressure difference as an indication of diaphragmatic contraction using catheters, balloons, or sensors in the esophagus and stomach. These methods are very invasive and uncomfortable, and not suitable for prolonged use or use during natural sleep.

Other prior art includes measurement of the electrical activation of various respiratory muscles, for example, the diaphragm, intercostal muscles, or various respiratory accessory muscles such as the alae nasi muscles.

Additional prior art uses various detectors of ribcage or abdominal movement, including inductance pneumograms, strain gauges, magnetometers, pneumatic belts, and the like.

The prior art most directly relevant to the present invention noninvasively estimates changes in pleural pressure by measuring the resultant deformation of the suprasternal notch. One known method teaches directly measuring the deformation of the skin of the suprasternal notch with a rigid mechanical probe in contact with the skin, and connected to a strain gauge or similar sensor of movement anchored to the sternum. U.S. Pat. No. 4,180,059 in the name of Tiep describes using a rigid mechanical probe in contact with the skin. Deformation of the skin by changing pleural pressure causes movement of the rigid probe, and thereby activation of the strain gauge or other position sensor. A disadvantage of this method is the need to have the probe actually touching the skin, which makes the device both mechanically difficult to position, and annoying to the subject.

A second known method uses a strip of piezo-electric material such as PVDF glued to the skin of the suprasternal notch. Deformation of the skin causes deformation of the PVDF, resulting in an electric charge developing between upper and lower surfaces which may then be measured. This method does not give good signals at low effort, and the finite input impedance of the charge amplifier results in a short time constant. It also requires the strip to be glued into the suprasternal notch, which is inconvenient for longterm use.

BRIEF DESCRIPTION OF THE INVENTION

The invention teaches the use of an optical sensor to measure movement of the skin of the suprasternal notch, this movement being a measure of respiratory effort. The invention further teaches the use of a trough detector with a time constant long compared with a breath but short compared with the interval between changes in body position, to detect the optical signal corresponding to zero effort, and to subtract the trough signal from the optical signal to produce a self-zeroing effort signal which automatically compensates for changes in body position. The invention yet further teaches co-mounting of the sensor with any required electronics, and sending the effort signal to a radio receiver by telemetry. Finally, the invention teaches the use of a soft, low irritant adhesive material which may be left in place on the skin for several days, the sensor being placed and removed as often as desired, without injuring the skin.

BRIEF DESCRIPTION OF THE FIGURES

FIG. 4 shows the response of the processing electronics of FIG. 3 to a shift in the signal at minimum effort due, for example, to body movement.

DETAILED DESCRIPTION OF THE INVENTION

Figure 1:
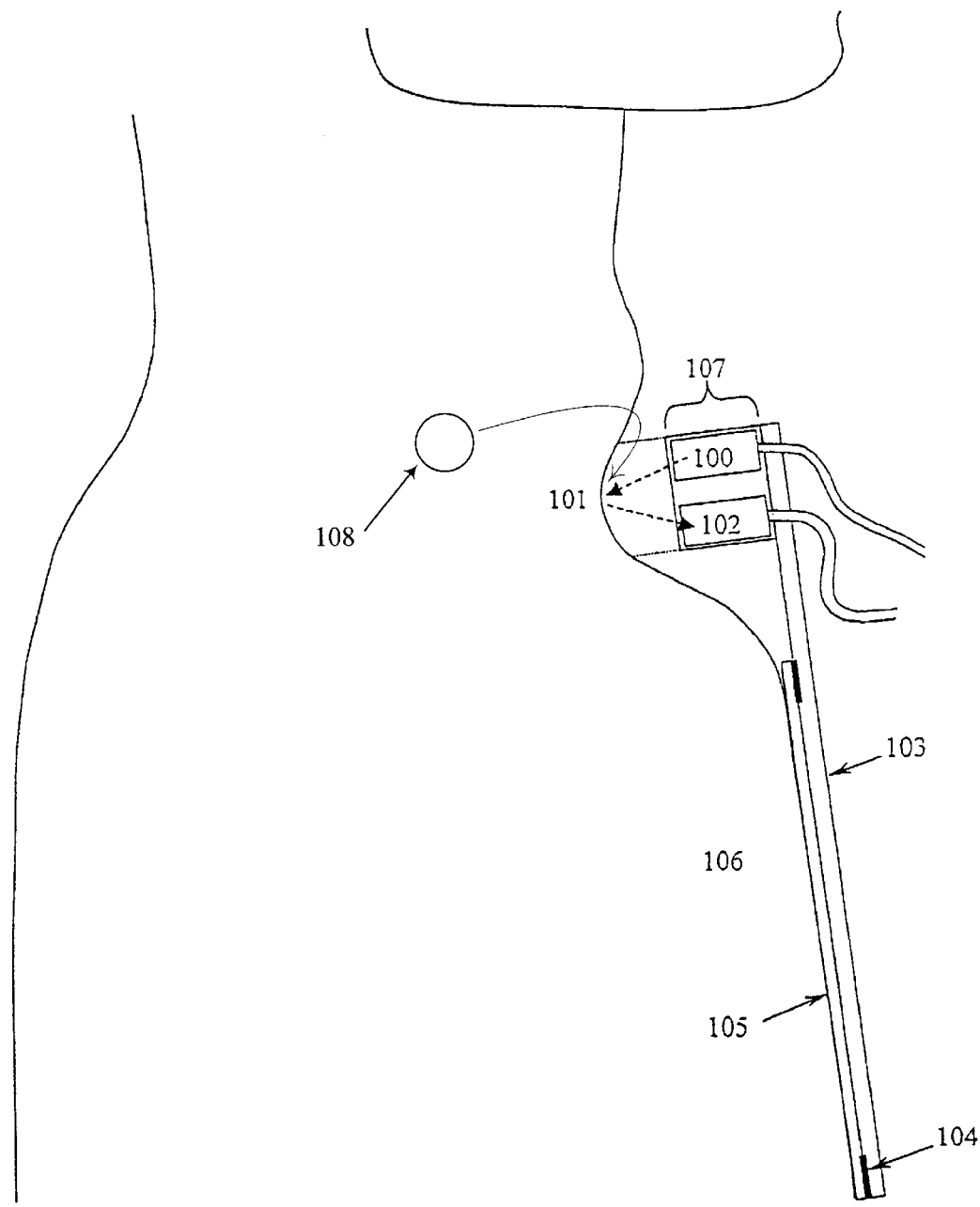
FIG. 1 depicts the illustrative embodiment of the invention, an optical sensor 107 mounted on the sternum 106, so that the output signal is influenced by the movement of the skin of the suprasternal notch 101.
Figure 1A:
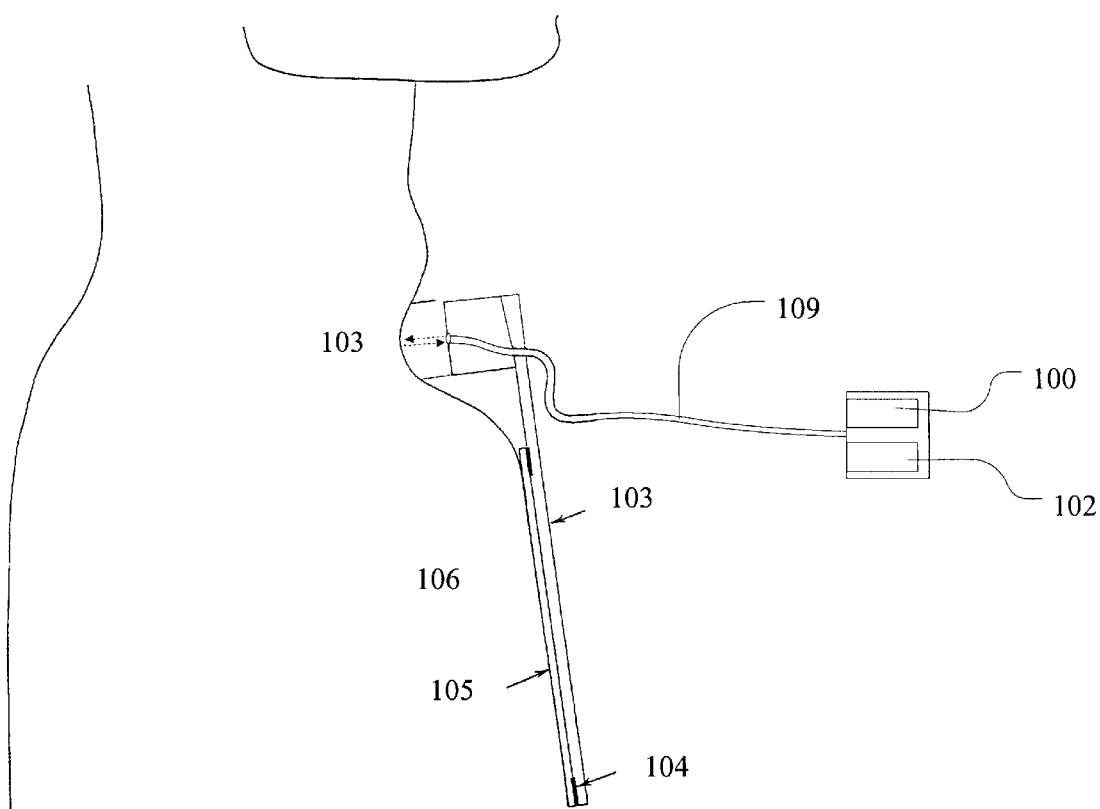
FIG. 1a shows one embodiment of the invention using a fibre optic cable.
Figure 1B:
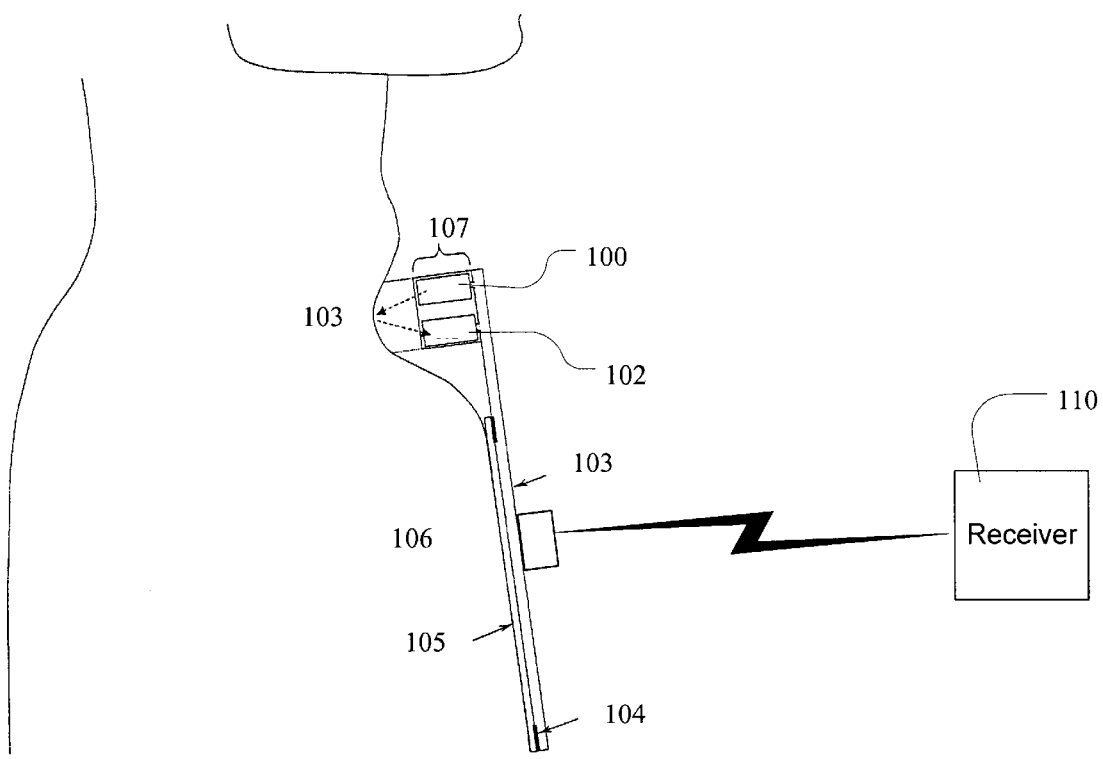
FIG. 1b illustrates an embodiment of the invention in which a signal from the sensor is relayed by telemetry to a receiver.

The present invention uses an optical sensor, such as an infrared proximity sensor, to measure the depth of the suprasternal notch, as shown in FIG. 1. A light source 100 shines light on the skin of the suprasternal notch 101, and the reflected light is received by photocell 102. (The term "photocell" is used to refer to any device whose output is light sensitive, e.g., a photodiode, phototransistor, etc.) The combined sensor assembly 107 may be mounted on any surface which is relatively immobile with respect to the skin of the suprasternal notch, such as the sternum 106. A suitable method for attachment is to mount the sensor 107 on cantilever 103, which is then adhered to the sternum using double-sided adhesive tape 104.

Preferably, the double-sided adhesive tape is not adhered directly to the skin, but is glued to a layer of soft, spongy, low irritant, low allergenic self-adhesive material 105. A suitable material is DuoDERM®, available from ConvatTec, of Princeton, N.J. The sensor is mounted such that the optical paths of light source and photocell are approximately normal to and centered over the skin at the deepest point of the suprasternal notch. The advantage of the layer of Duo-DERM is that it can remain in place on the skin for long periods, and the sensor can be removed and reapplied multiple times without trauma to the skin. Cantilever 103 can itself be made from a semi-flexible material, such as foam or silicone rubber with embedded aluminium reinforcing, so that it can be bent to conform to suit the subject and adjust the distance from the skin of the suprasternal notch. Alternatively, or in addition, sensor 107 can be mounted on the cantilever with adjusting screws so as to adjust the distance of the sensor from the skin of the suprasternal notch. To gain a lower profile, it is convenient to have the optical axis of the sensor parallel with the sternum and use a small mirror to direct the light path at the skin of the suprasternal notch. Another low profile arrangement is to surface mount the sensor electronic components directly onto the cantilever.

Small to moderate inspiratory and expiratory efforts cause quasi-linear movement of the skin of the suprasternal notch, with inspiratory efforts causing the skin to be sucked inwards, away from the sensor, and active expiratory efforts to cause the skin to bulge outwards, towards the sensor. Progressively larger efforts cause progressively smaller increments in skin movement, and efforts of more than about ±10 to 20 $cmH_2O$ pleural pressure produce little further change in the signal. This is convenient, because small efforts produce measurable deformations in the skin, and it is desired to detect small efforts.

Figure 2:
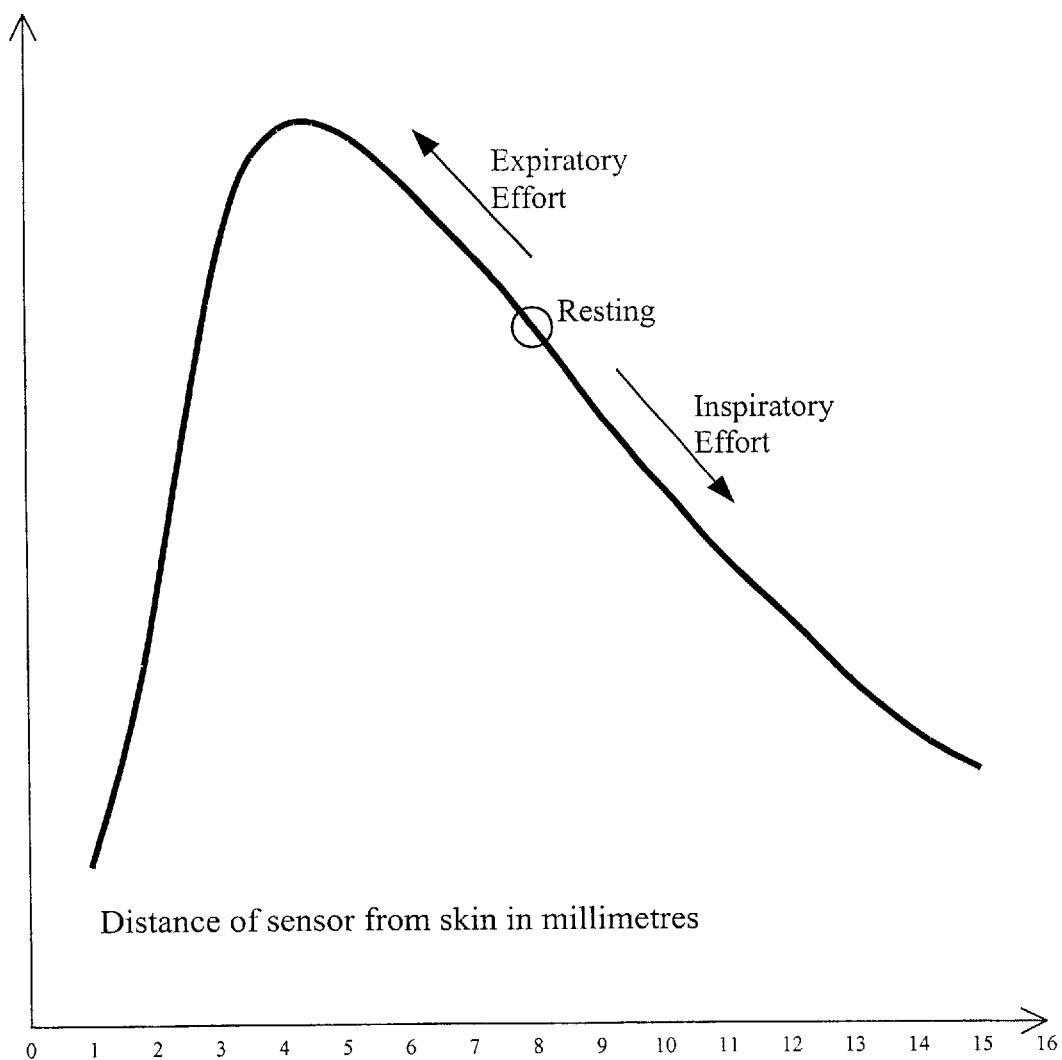
FIG. 2 shows a graph of light current from a commercially available optical sensor as a function of distance between the front of the sensor and the skin. The graph shows how if the sensor is placed at approximately 8 mm from the skin of the suprasternal notch, the signal decreases as the skin is sucked away from the sensor with inspiratory effort, and the signal increases as the skin bulges towards the sensor with expiratory effort.

In a preferred arrangement, the light source 100 of the sensor is an infrared light emitting diode, and the photocell 102 of the sensor is a photoresistor, photodiode, or phototransistor. For example, using a commercially available EE-SF5 photomicrosensor available from Omron Corporation, of Kyoto, Japan, the electrical output (light current) increases quasi-linearly for distances from zero to about 4 millimetres, and then decreases quasi-exponentially for distances greater than 5 millimetres, as shown in FIG. 2. (At short distances, a reduced amount of light is detected because of light angle considerations.) Therefore, in the preferred embodiment, the sensor assembly is placed so that the front face of the combined sensor 107 is approximately 8 millimetres from the skin. Inspiratory efforts will cause the distance to increase, resulting in a quasi-exponentially decreasing electrical signal, and expiratory efforts will cause an increasing signal.

In an alternative embodiment, the sensor could be positioned and sized such that it is the ascending portion of the curve of FIG. 2 that is operative, with the light current output increasing with increasing distance.

It is also possible not to glue the cantilever to the skin, but to hold it in place using a bandage, harness, or similar mechanism. Alternatively, the cantilever may be attached to a tight stretch garment such as a Lycra® T-shirt. Combining both alternatives, the cantilever may be mounted on a large disc of soft, thin, high-friction material such as silicone, typically 10 centimeters in diameter, which may be held by friction in contact with the skin by a harness, bandage, stretch Lycra T-shirt, etc. A very low durometer silicone will tend to have a higher coefficient of friction. The large, soft, thin, disc of high friction material may be perforated with multiple holes in order to allow the skin to breathe.

Normally, inspiratory effort is active and expiration is passive. In the preferred embodiment discussed so far using the EE-SF5 sensor, inspiratory effort causes a decreasing light current, as shown in FIG. 2. Therefore, for convenience, the output from the photosensor 102 is inverted, so that inspiration produces a positive signal. This signal is then amplified and zero-adjusted so that zero effort produces an output signal of zero. Changes in posture will tend to change the distance between sensor and skin, which will change the output voltage for zero effort. It is desirable to automatically adjust for such changes in posture, so that zero effort once again produces zero output signal.

If the optical sensor has been set up so that a positive signal corresponds to inspiratory effort, and if the patient is not making active expiratory efforts, the minimum signal during a breath will correspond to zero effort. A trough detector, comprising a capacitor charged by the sensor output via a resistor, and discharged by the sensor output via a diode, with the resistor-capacitor time constant long compared with a breath but short compared with the interval between postural changes, will track this minimum effort. A suitable time constant is ten seconds. Preferably, the diode is in the feedback loop of an operational amplifier to provide correct operation close to zero signal. A subtractor operational amplifier then subtracts the output of the trough detector from the output from the sensor to yield the effort signal.

Figure 3:
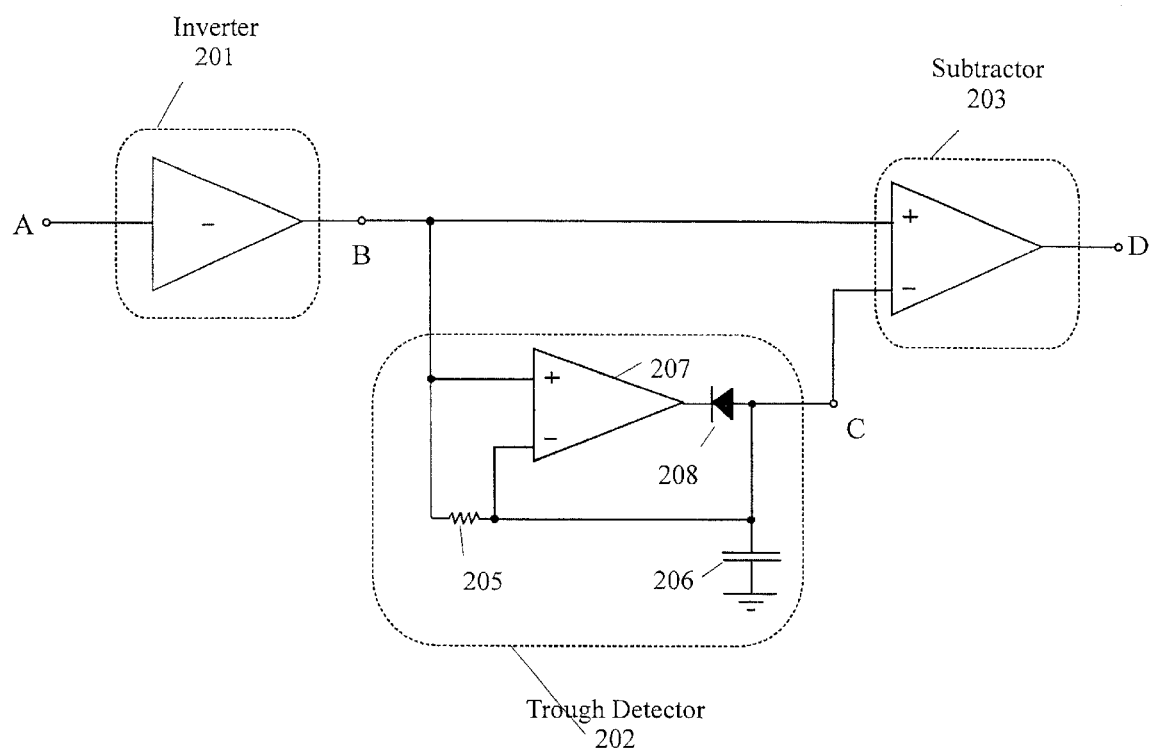
FIG. 3 is a block diagram of processing electronics, including a trough detector to track changes in the light signal even in the presence of body movement, and a subtractor to remove such changes from the signal.

A suitable circuit block diagram for the entire assembly is shown in FIG. 3. Point (A) is the output from a phototransistor or other light-responsive detector, point (B) is the output after inversion by inverter 201, point (C) is the output from the trough detector 202, and point (D) is the zero-corrected effort signal output. FIG. 4 shows the action of the entire assembly. The top tracing is a simulated true respiratory effort, as might be measured using an esophageal pressure transducer, recorded for a period of 4 minutes, or 60 breaths. The peak inspiratory effort varies in amplitude with a period of 30 seconds. The second tracing shows the signal from the phototransistor, at point (A). This signal is upside down, because increasing effort causes the skin to recede from the sensor, causing a reduction in light current from the phototransistor. Zero effort is represented by the thick dashed horizontal line which runs along the top of the tracing.

During the second of the four minutes, the DC offset changes, to simulate the effect of a change in posture leading to the sensor being held closer to the skin (more light output) at zero effort. The third tracing shows the signal at point (B), after inversion. The heavy line on the fourth tracing shows the signal at point (C), which is the output of the trough detector. For convenience, the signal at point (B) is reproduced as a thin line along with the output of the trough detector. The trough detector tracks the DC shift in the signal during the second minute of the tracing. The reason for this is as follows.

Capacitor 206 charges through resistor 205 to the potential at point (B). If the potential at point (B) rises above that of the capacitor, the potential at the output of operational amplifier 207 will be greater than that of the capacitor, and diode 207 will be reverse biased. The capacitor potential rises slowly through resistor 205 to the potential at point (B), but it takes several breaths for this to happen. But if the input at point (B) drops below the capacitor level, operational amplifier 207 conducts current through the diode. The capacitor voltage thus decreases rapidly to the lowest level of the input.

The output at point (D) is shown in the bottom tracing—it is the difference (formed in subtractor 203) of the signal at point (B) and the heavy line shown in the tracing for the signal at point (C). The net result is that the final output signal at point (D) is zero for zero effort (along the horizontal axis of the tracing), even if the light output changes due to a change in posture, and the signal increases with increasing effort.

The above functionality can also be performed by a microprocessor which executes a program that samples the sensor output signal, tracks the minimum signal over a time period long compared with a breath but short compared with the interval between body movements (such as 10 seconds), and subtracts the minimum signal from the sensor output signal to yield the effort signal.

The color of the skin somewhat influences the reflectivity of the suprasternal notch. Furthermore, the descent of the cricoid cartilage into the upper part of the suprasternal notch can somewhat attenuate the signal. A larger and more reproducible signal, less influenced by skin color or movement of the cricoid may be obtained by placing a small self-adhesive disc 108 of material of known reflectance, for example, white paper or aluminium foil, on the skin at the deepest point of the suprasternal notch.

Although no part of the electrical circuit touches the skin, for reasons of electrical safety the sensor assembly, cable, and electronics may be doubly insulated or, alternatively, the light source and photocell may be placed well away from the patient, and the light source and photocell connected to the skin via optical fibre. By using a semi-reflecting prism, the light source, which can be a low powered laser, and the photosensor can share the same optical fibre cable 109. Alternatively, the light source and photocell may be battery operated, and the signal from the photocell may be relayed to a distant receiver 110 by telemetry.

The optimum position for the sensor is so that the point of reflection of the light beam is that part of skin of the suprasternal notch which moves the most in an anteroposterior direction. In general this will be the deepest part of the suprasternal notch.

The sensor assembly 107 preferably has a low profile to avoid double chins.

Although the invention has been described with reference to a particular embodiment, it is to be understood that this embodiment is merely illustrative of the application of the principles of the invention. For example, the invention may be adapted for use with children. Thus it is to be understood that numerous modifications may be made in the illustrative embodiment of the invention and other arrangements may be devised without departing from the spirit and scope of the invention.

What is claimed is:

1. A method for measuring respiratory effort comprising the steps of mounting an optical sensor on a patient's body, adjusting the position of the optical sensor so that movement of the skin of the suprasternal notch produces a change in the output signal of the optical sensor, directing light to the suprasternal notch and detecting light reflected therefrom, wherein the optical sensor is a light source for directing light to the suprasternal notch and a photocell for detecting light reflected therefrom.

2. A method in accordance with claim 1 wherein the light source is an infrared light source.

3. A method in accordance with claim 1 wherein the optical sensor is a photodiode, phototransistor, or photoresistor.

4. A method in accordance with claim 1 wherein the step of mounting uses an adhesive.

5. A method in accordance with claim 1 wherein the step of mounting includes gluing a first low-irritant mounting component to the skin using low-irritant materials, the first component being for attachment to a second mounting component on the optical sensor.

6. A method in accordance with claim 1 wherein the step of mounting employs a bandage, harness, or T-shirt to hold a mounting for the optical sensor in contact with the skin by friction.

7. A method in accordance with claim 6 wherein a portion of the mounting that is in direct contact with the skin is a large, thin, flexible, high coefficient-of-friction material.

8. A method in accordance with claim 7 wherein said material is of soft silicone.

9. A method in accordance with any of claims 1–8 further comprising placing a self-adhesive disc of highly reflecting material in the suprasternal notch.

10. A method in accordance with any of claims 1–8 further comprising locating the optical sensor remotely from the patient, and guiding the light by a fibre optic cable to and from the skin.

11. A method in accordance with any of claims 1–8 further comprising relaying the optical sensor output signal by telemetry.

12. A method in accordance with any of claims 1–8 further comprising processing the signal from the optical sensor so that (1) increasing inspiratory effort yields an increasingly positive signal, (2) a minimum signal during a breath is detected using a trough detector with a time contstantlong compared with a breath but short compared with the interval between body movements, and said minimum signal is subtracted from the processed optical sensor signal to provide an effort signal.

13. A method for measuring a patient's respiratory effort by using an optical sensor mounted on the patient's body, the optical sensor directing light to the patient's suprasternal notch and detecting the light reflected therefrom, the optical sensor being mounted on the patient's body so as not to move with the skin of the suprasternal notch such that relative movement between the optical sensor and the suprasternal notch produces a change in an output signal of the optical sensor.

14. A method in accordance with claim 13 further comprising the step of mounting the optical sensor on skin over the manubrium or the sternum.

15. A method in accordance with claim 14 wherein the mounting step is performed by adhering the sensor on the skin using an adhesive.

16. A method in accordance with any of claims 13–15 further comprising the steps of gluing a first low-irritant mounting component to the patient's skin using low-irritant materials, and attaching a second mounting component on the optical sensor to the first mounting component.

17. A method in accordance with any of claims 13–15 further comprising the step of processing the signal from the optical sensor to render it independent of body movement.

18. A method in accordance with any of claims 13–15 further comprising processing the signal from the optical sensor so that (1) increasing inspiratory effort yields an increasingly positive signal, (2) a minimum signal during a breath is detected using a trough detector with a time constant long compared with a breath but short compared with an interval between body movements, and (3) said minimum signal is subtracted from the processed optical sensor signal to provide an effort signal.

19. A device for measuring a patient's respiratory effort comprising an optical sensor mountable on the patient's body, the optical sensor directing light to the patient's suprasternal notch and detecting the light reflected therefrom, the optical sensor being mountable on the patient's body so as not to move with the skin of the suprasternal notch such that relative movement between the optical sensor and the suprasternal notch produces a change in an output signal of the optical sensor; and.means to automatically maintain the output signal corresponding to zero effort to be zero, independently of non-breathing related body changes.

20. A device in accordance with claim 19 further comprising an adhesive for mounting the optical sensor on skin over the manubrium or the sternum.

21. A device in accordance with claim 20 further comprising a first low-irritant mounting component glued to the patient's skin using low-irritant materials, and a second mounting component for attaching the optical sensor to the first mounting component.

22. A device in accordance with claim 21 further comprising a means for processing the signal from the optical sensor so that increasing inspiratory effort yields an increasingly positive signal, a minimum signal during a breath is detected using a trough detector with a time constant that is long compared with a breath but short compared with the interval between body movements, and said minimum signal is subtracted from the processed optical sensor signal to provide an effort signal.

23. A device in accordance with any of claims 22 further comprising a means for processing the signal from the optical sensor so that increasing inspiratory effort yields an increasingly positive signal, a minimum signal during a breath is detected using a trough detector with a time constant that is long compared with a breath but short compared with the interval between body movements, and said minimum signal is subtracted from the processed optical sensor signal to provide an effort signal.

* * * * *

UNITED STATES PATENT AND TRADEMARK OFFICE
CERTIFICATE OF CORRECTION

PATENT NO. : 6,445,942 B1
DATED : September 3, 2002
INVENTOR(S) : Michael Berthon-Jones et al.

It is certified that error appears in the above-identified patent and that said Letters Patent is hereby corrected as shown below:

Title page,
Item [73], Assignee, should read as follows:
-- RESMED LTD.
   97 Waterloo Road
   North Ryde NSW, Australia 2113 --

Signed and Sealed this

Twenty-seventh Day of July, 2004

JON W. DUDAS
*Acting Director of the United States Patent and Trademark Office*